United States Patent
Searfoss et al.

(10) Patent No.: US 11,992,673 B2
(45) Date of Patent: *May 28, 2024

(54) IMPLANTABLE MEDICAL DEVICES AND METHODS OF MANUFACTURE

(71) Applicant: Oscor Inc., Palm Harbor, FL (US)

(72) Inventors: Timothy Searfoss, New Port Richey, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/479,745

(22) Filed: Sep. 20, 2021

(65) Prior Publication Data

US 2022/0001169 A1 Jan. 6, 2022

Related U.S. Application Data

(63) Continuation of application No. 16/003,881, filed on Jun. 8, 2018, now Pat. No. 11,147,963.

(60) Provisional application No. 62/517,444, filed on Jun. 9, 2017.

(51) Int. Cl.
*A61N 1/05* (2006.01)

(52) U.S. Cl.
CPC ..................... *A61N 1/05* (2013.01)

(58) Field of Classification Search
CPC ....................................... A61N 1/05
See application file for complete search history.

(56) References Cited

U.S. PATENT DOCUMENTS

| | | | |
|---|---|---|---|
| 5,074,313 A | 12/1991 | Dahl et al. | |
| 5,324,327 A * | 6/1994 | Cohen | A61N 1/056 977/932 |
| 5,935,159 A * | 8/1999 | Cross, Jr. | A61N 1/056 607/116 |
| 7,130,700 B2 | 10/2006 | Gardeski et al. | |
| 2002/0143377 A1 | 10/2002 | Wessman et al. | |
| 2004/0097965 A1 | 5/2004 | Gardeski et al. | |
| 2006/0142652 A1 | 6/2006 | Keenan | |
| 2009/0005825 A1 * | 1/2009 | MacDonald | A61N 1/0563 607/5 |
| 2009/0276021 A1 * | 11/2009 | Meadows | H01R 43/00 607/116 |
| 2010/0030291 A1 | 2/2010 | Havel et al. | |
| 2011/0130817 A1 | 6/2011 | Chen | |
| 2011/0130818 A1 | 6/2011 | Chen | |
| 2012/0025344 A1 | 10/2012 | Osypka | |
| 2015/0021817 A1 | 1/2015 | Romero et al. | |
| 2016/0279409 A1 * | 9/2016 | Govea | A61N 1/3752 |

(Continued)

*Primary Examiner* — Mallika D Fairchild
(74) *Attorney, Agent, or Firm* — Michael F. Scalise (57) ABSTRACT

A method for manufacturing an implantable lead includes forming an elongated lead body core that defines a longitudinal axis. The elongated lead body core has a plurality of axially extending channels that are circumferentially spaced apart from one another around the elongated lead body core. The method also includes positioning an electrode ring around the elongated lead body core and electrical conductors. The method includes positioning a respective electrical conductor in each of the axially extending channels and positioning a dielectric insulator ring around the elongated lead body core and electrical conductors.

19 Claims, 8 Drawing Sheets

(56) References Cited

U.S. PATENT DOCUMENTS

2017/0080215 A1     3/2017  Osypka
2017/0312500 A1*   11/2017  Shoberg ............... A61N 1/0551

* cited by examiner

IMPLANTABLE MEDICAL DEVICES AND METHODS OF MANUFACTURE

CROSS-REFERENCE TO RELATED APPLICATION

This application is a continuation application of U.S. patent application Ser. No. 16/003,881, filed on Jun. 8, 2018, now U.S. Pat. No. 11,147,963, which claims the benefit of priority to U.S. Provisional Patent Application No. 62/517,444, filed Jun. 9, 2017. All of the above-mentioned applications are incorporated by reference herein in their entirety.

BACKGROUND OF THE INVENTION

1. Field of the Invention

The subject disclosure relates to implantable medical devices, and more particularly, to implantable leads that include conductors and contacts.

2. Description of Related Art

Multipolar implantable leads are used for neuro-stimulation to treat certain chronic diseases such as chronic pain, incontinence, Parkinson, depression, and epilepsy. Traditional multipolar implantable leads have multiple electrodes, in most cases a minimum of 4, and in many cases up to 8 or 16 electrodes, which all have to be connected with a conductor of some type but in most cases by a stranded cable (1×19 or 9×9). The leads have very small lead bodies, commonly smaller than 4 French (F) (1.35 mm) in diameter, and have to be isodiametric.

Lead bodies often include a lumen for each conductor to be separately housed. The lead body and areas of dielectric isolation are often manufactured by using a multilumen extrusion. To keep the lead isodiametric, certain areas on the lead body where the actual stimulation electrodes are positioned are getting laser ablated so the electrodes can be stacked up and aligned along the lead body. This process tends to be time consuming and expensive. Specifically, the laser ablation of such small lead body tubing has to be extremely precise as the dimensions of the tubing itself, and the areas to be removed by method of ablation are very small. The precision required with laser ablation can result in a very slow production process.

The conventional techniques have been considered satisfactory for their intended purpose. However, there is an ever present need for improved lead bodies and improved methods of manufacture.

SUMMARY OF THE INVENTION

A method for manufacturing an implantable lead includes forming an elongated lead body core that defines a longitudinal axis. The elongated lead body core has a plurality of axially extending channels that are circumferentially spaced apart from one another around the longitudinal axis of the elongated lead body core. The method includes positioning a respective electrical conductor in each of the axially extending channels. The method includes positioning an electrode ring around the elongated lead body core and at least one of the conductors. The method includes positioning a dielectric insulator ring around the elongated lead body core and adjacent to the electrode ring.

In accordance with some embodiments, the method includes heating the elongated lead body core and the dielectric insulator ring to bond the elongated lead body core and the dielectric insulator ring together.

The method can include positioning additional dielectric insulator rings and electrode rings around the elongated lead body core. It is contemplated that positioning the additional dielectric insulator rings and electrode rings can include positioning them in an axially alternating pattern.

The method can include bonding the electrode ring to at least one of the conductors.

Forming the elongated lead body core can include forming the elongated lead body core by extrusion. The elongated lead body core can include an inner central lumen.

The method can include positioning a dielectric end cap on a distal end of the elongated lead body core and/or a proximal end of the elongated lead body core. It is contemplated that the method can include heating the elongated lead body core and the dielectric end cap to bond the elongated lead body core and dielectric end cap together. The method can include positioning a dielectric sleeve around the elongated lead body core. The dielectric sleeve and/or the dielectric insulator ring can be formed by extrusion.

In accordance with another aspect of the invention, an implantable lead includes an elongated lead body core that defines a longitudinal axis. The elongated lead body core is similar to that formed by the method described above and includes axially extending channels as described above. Respective electrical conductors are in each of the axially extending channels. An electrode ring is positioned around the outer periphery of the elongated lead body core and at least one of the electrical conductors. A dielectric insulator ring is positioned around an outer periphery of the elongated lead body core adjacent to the electrode ring.

Additional dielectric insulator rings and electrode rings can be positioned around the elongated lead body core. It is contemplated that the dielectric insulator rings can be longitudinally spaced apart from one another, and a respective one of the electrode rings can be positioned between two of the longitudinally adjacent spaced apart dielectric insulator rings. The electrode ring can be bonded to at least one of the conductors. A dielectric end cap can be positioned on a distal end and/or a proximal end of the elongated lead body core. A dielectric sleeve can be positioned around the elongated lead body core.

These and other features of the subject invention and the manner in which it is manufactured, assembled and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
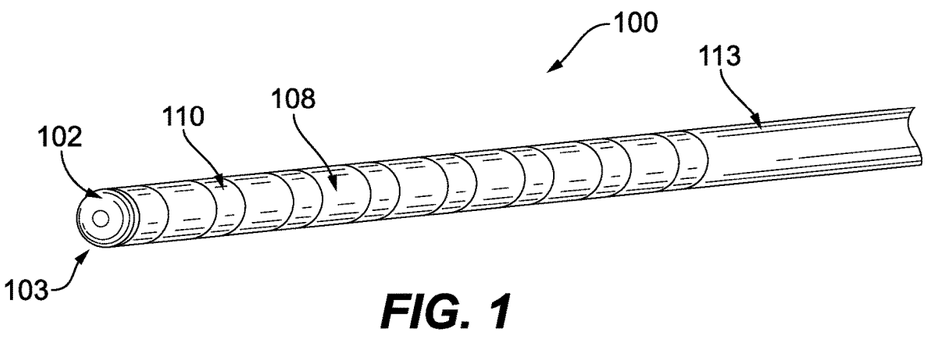
FIG. 1 is a schematic perspective view of a distal end portion of an implantable medical device, showing dielectric insulator rings positioned between axially adjacent spaced apart electrode rings.
Figure 12:
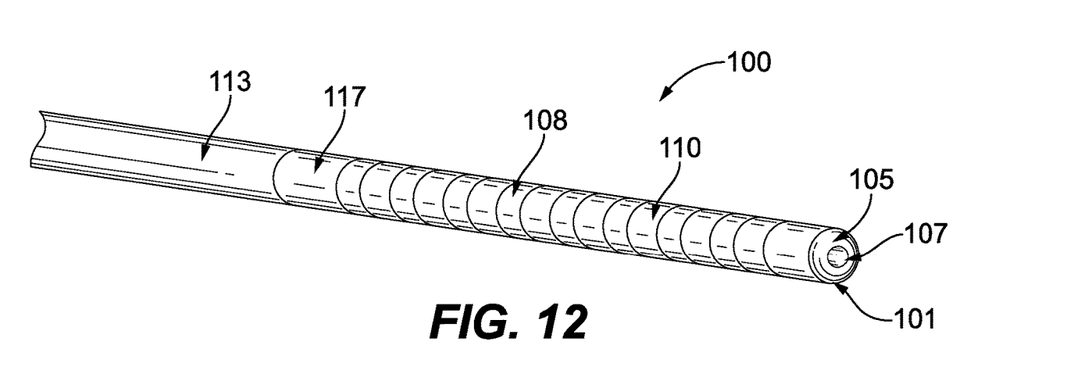
FIG. 12 is a schematic perspective view of a proximal end portion of the implantable medical device of FIG. 1, showing a similar construction to that of the distal end.

Referring now to the drawings wherein like reference numerals identify similar structural features and/or elements of the subject matter disclosed herein, there is illustrated in FIG. 1 a distal end 103 of an implantable lead 100. A proximal end 101 of the implantable lead 100 is shown in FIG. 12. Proximal end 101 has a configuration similar to distal end 103 and can be inserted into an active medical stimulator device, or the like, as disclosed for example in commonly assigned U.S. Patent Application Publication 2012/0253445, the disclosure of which is herein incorporated by reference in its entirety. Embodiments described herein address the issues with the precision required in manufacturing implantable leads. Embodiments of the disclosure provide a manufacturing process that avoids the manufacturing complexities associated with laser ablating small lead body tubing, resulting in an implantable lead that can be manufactured in less time and for reduced cost.

Figure 2:
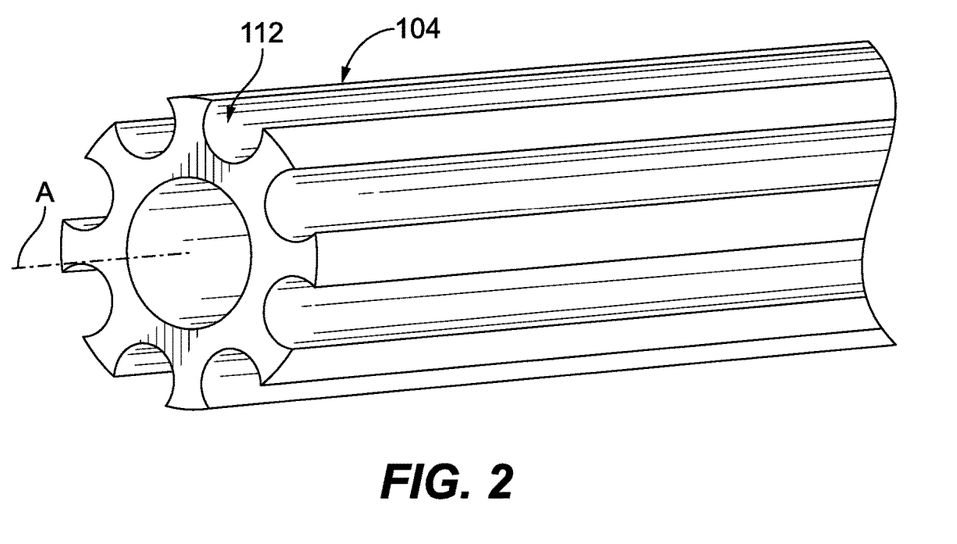
FIG. 2 is a schematic perspective view of a distal end portion of an elongated lead body core of the implantable medical device of FIG. 1, showing axially extending channels and an axially extending lumen.
Figure 3:
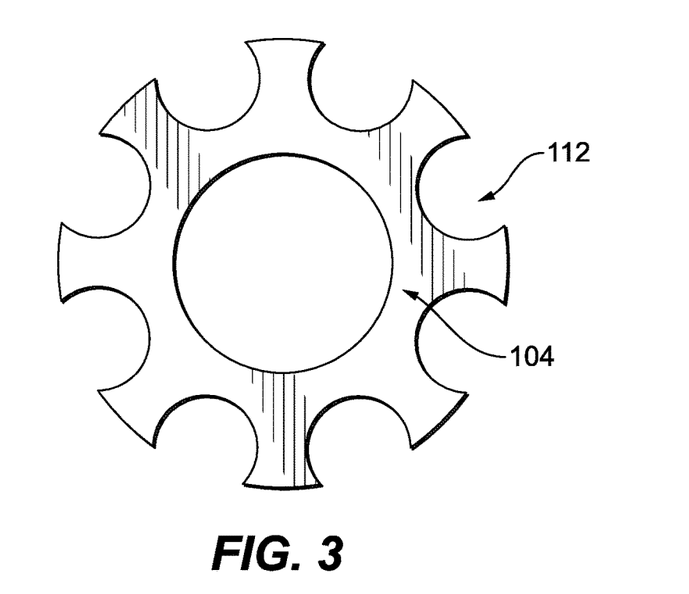
FIG. 3 is a schematic plan view of the distal end of the elongated lead body core of FIG. 2.
Figure 13:
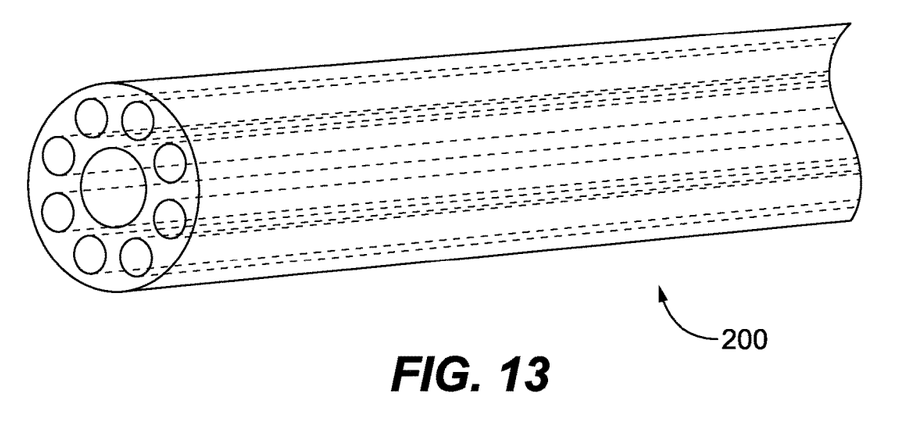
FIG. 13 is a schematic perspective view of an extruded lead body core with enclosed lumen for each conductor to be separately housed.
Figure 14:
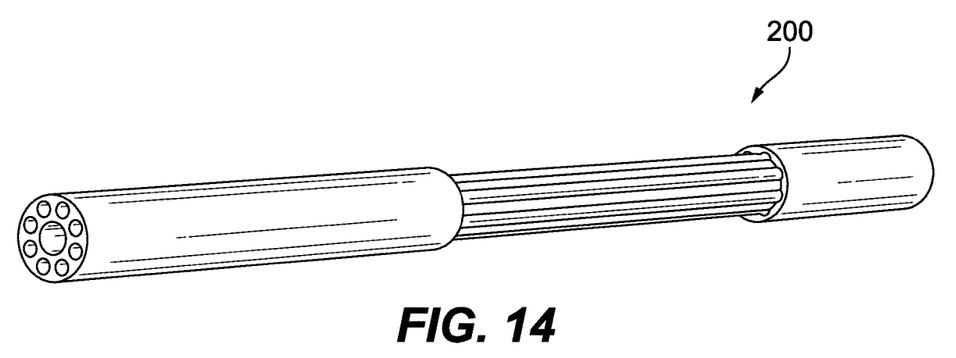
FIG. 14 is a schematic perspective view of the extruded lead body core of FIG. 13, with a portion of the outer diameter laser ablated so the electrodes can be stacked up and aligned along the lead body.

As shown in FIG. 1, distal end 103 of implantable lead 100 includes dielectric insulator rings 108 positioned between axially adjacent spaced apart electrode rings 110. An end cap 102 covers distal tip of implantable lead 100. Implantable lead 100 also includes a dielectric insulator sleeve 113. With reference now to FIGS. 2-3, implantable lead 100 is formed with an elongated lead body core 104 that defines a longitudinal axis A. FIGS. 2-3 show a distal end of elongated lead body core 104. Those skilled in the art will readily appreciate that a proximal end portion of elongated lead body core 104 is similar to that of distal end 103. Elongated lead body core 104 has a plurality of axially extending channels 112 that are circumferentially spaced apart from one another around longitudinal axis A of elongated lead body core 104 and an inner central lumen extending therethrough. Lead body core 104 and its channels 112 are formed through extrusion, e.g. plastic extrusion. FIG. 2 shows lead body core 104 after extrusion. After extrusion, axially extending channels 112 are open, e.g. not enclosed by additional dielectric material like a body 200 of FIG. 13. The extrusion of the very small profile of lead body core 104 can be performed with extrusion tooling with a 2 to 4 draw down ratio. Due to this ratio, it is contemplated that the extrusion tooling can be manufactured by laser micro-machining. By forming lead body core 104 through extrusion, instead of forming the entire body including an outer diameter shell covering the channels through extrusion (as shown in prior art FIGS. 13 and 14), the need to laser ablate the outer diameter (as shown in FIG. 14) to make room for electrode rings 110 is avoided with lead body core 104. This reduces manufacturing time and cost and makes large scale production of implantable lead 100 easier.

Figure 4:
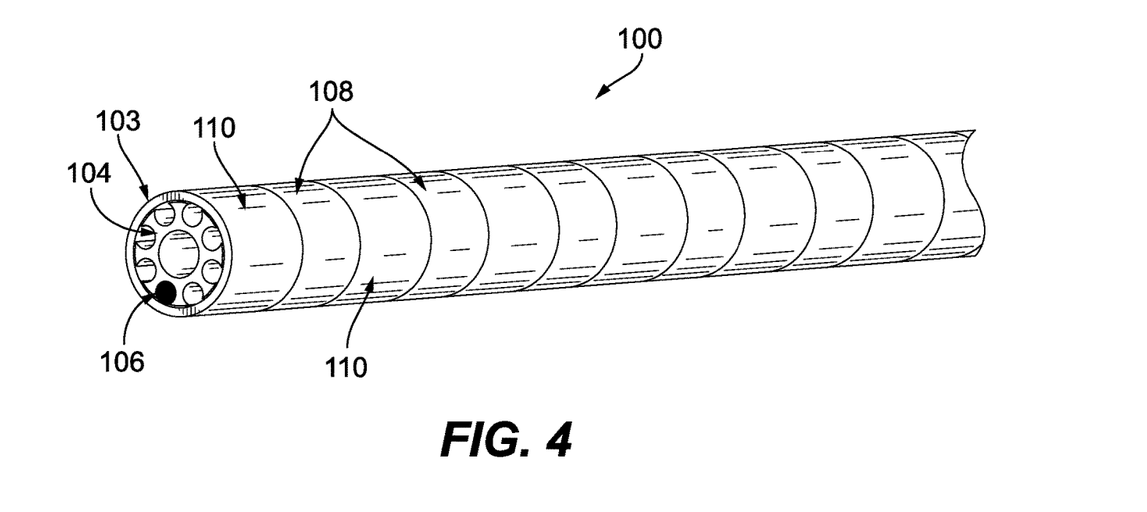
FIG. 4 is a schematic perspective view of the distal end portion of the implantable medical device of FIG. 1 with the end cap removed, showing an electrical conductor positioned within one of the axially extending channels of the elongated lead body core.

With reference now to FIG. 4, conductor 106 is positioned in respective axially extending channel 112. Axially alternating dielectric insulator rings 108 and electrode rings 110 are positioned around elongated lead body core 104 and electrical conductors 106. Any suitable number of dielectric insulator rings 108 and electrode rings 110 can be positioned around elongated lead body core 104.

Figure 5:
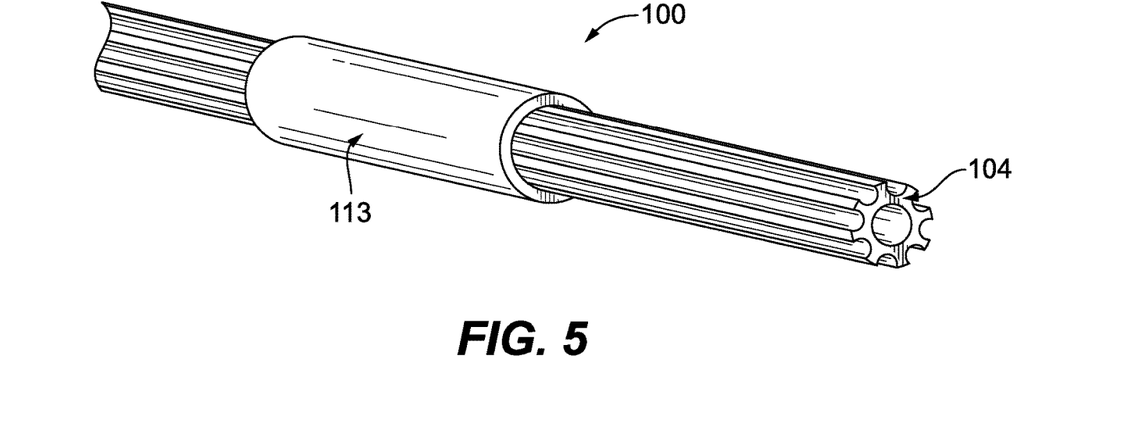
FIG. 5 is a schematic perspective view of the distal end of the elongated lead body core of FIG. 2, showing a dielectric insulator sleeve positioned over the elongated lead body core.
Figure 6:
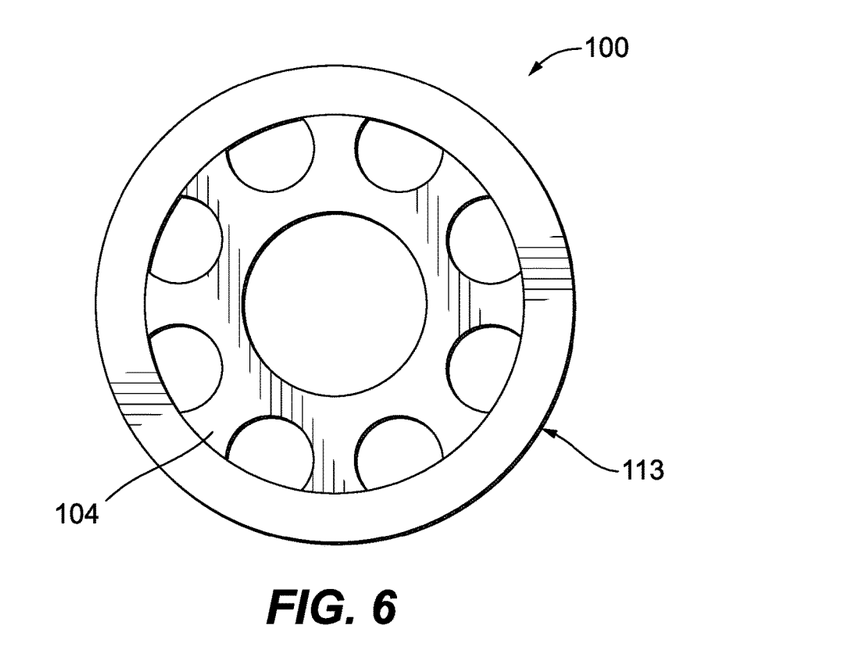
FIG. 6 is schematic a cross-sectional view of the distal end of the elongated lead body core of FIG. 2 and the dielectric insulator sleeve.
Figure 7:
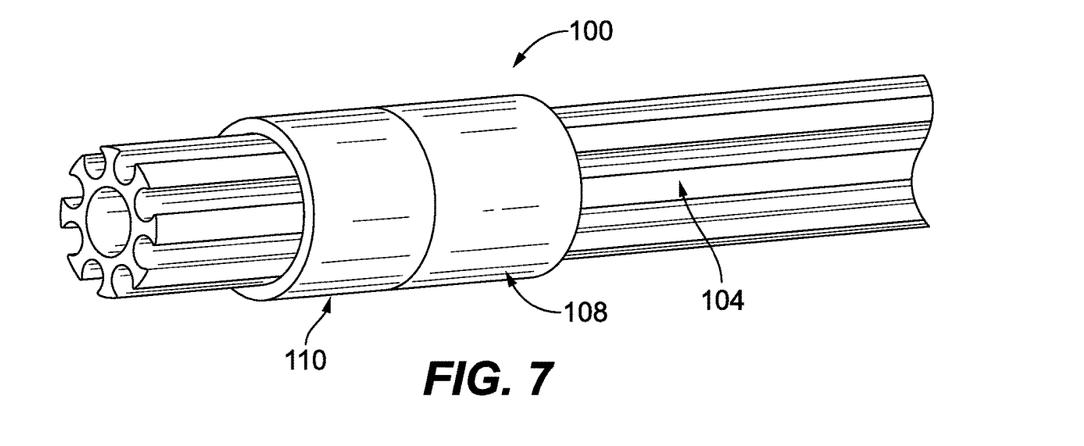
FIG. 7 is a schematic perspective view of a portion of the implantable medical device of FIG. 1, with a dielectric insulator ring and an electrode ring sliding over the outer periphery of the elongated lead body core as they are being positioned.

As shown in FIGS. 5-6, a dielectric insulator sleeve 113 is slid around the outer periphery of elongated lead body core 104, before electrical conductors 106 are positioned. Sleeve 113 encloses a portion of axially extending channels 112. With reference now to FIG. 7, one of dielectric insulator rings 108 and one of electrode rings 110 are slid around the outer periphery of elongated lead body core 104 as they are being positioned.

Figure 8:
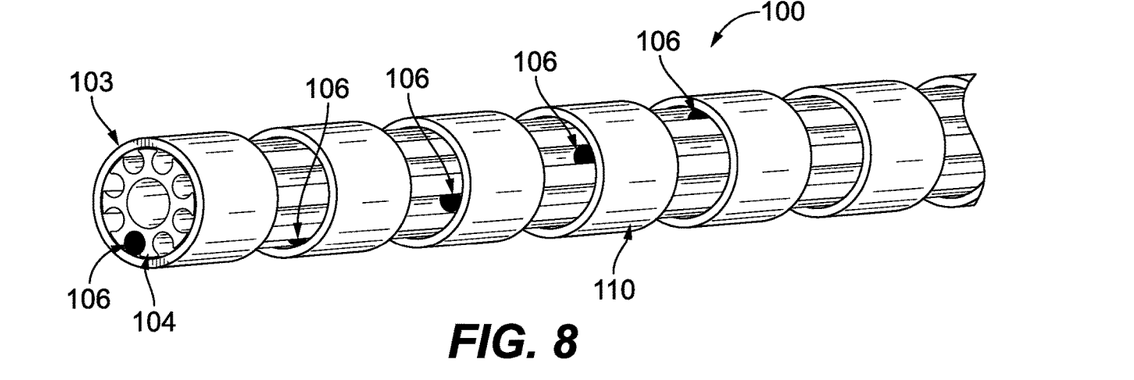
FIG. 8 is a schematic perspective view of a portion of the implantable medical device of FIG. 1, showing a series of axially spaced apart electrode rings positioned around the elongated lead body core and multiple conductors.

As shown in FIG. 8, a series of axially spaced apart electrode rings 110 are positioned around elongated lead body core 104 and multiple conductors 106. Conductors 106 are shown with shaded ends to distinguish between conductors 106 and their respective longitudinal channels 112. The gaps between electrode rings 110 are where dielectric insulator rings 108 are positioned. Dielectric insulator rings 108 are not shown for clarity.

Figure 9:
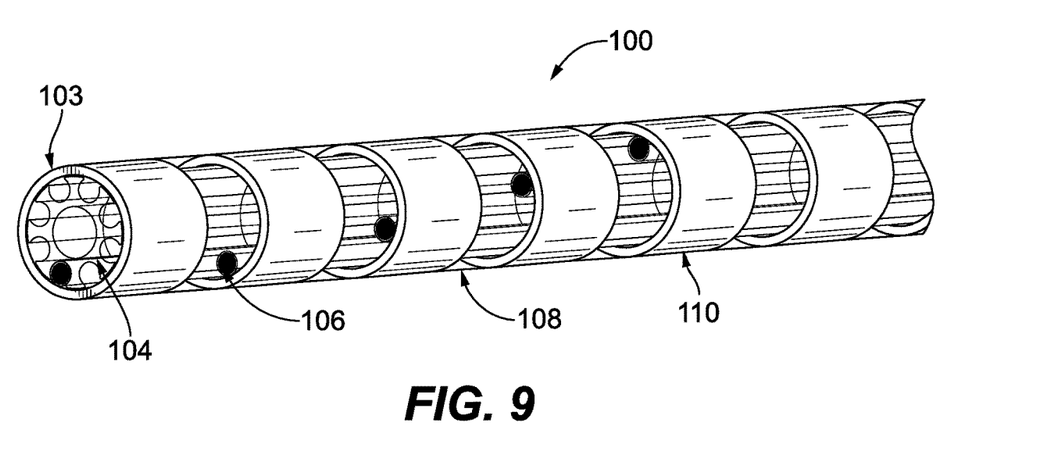
FIG. 9 is a schematic perspective view of a portion of the implantable medical device of FIG. 1, showing the dielectric insulator rings translucently so that the conductors are visible.

FIG. 9 shows implantable lead 100 of FIG. 1 without end cap 102. Elongated lead body core 104 and dielectric insulator rings 108 are shown translucently so that conductors 106 can be seen. Those having skill in the art will readily appreciate that elongated lead body core 104 and dielectric insulator ring 108 can be opaque, translucent or transparent.

Figure 10A:
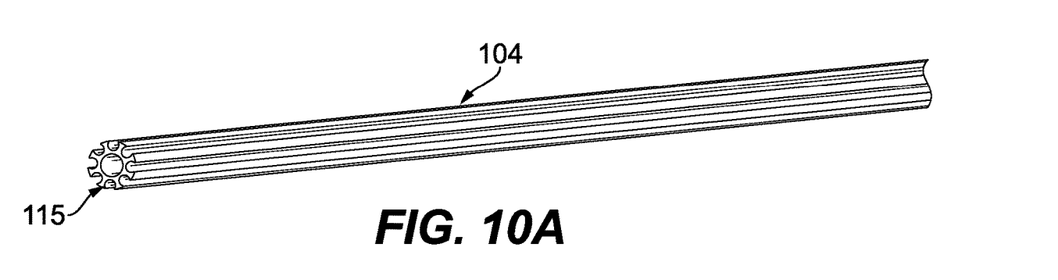
FIG. 10A is a schematic perspective view of a distal end portion of the elongated lead body core of the implantable medical device of FIG. 1, after extrusion.
Figure 10B:
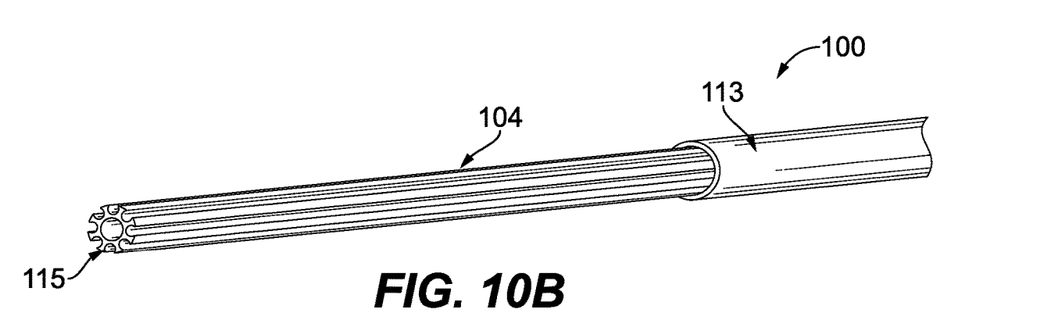
FIG. 10B is a schematic perspective view of a distal end portion of the elongated lead body core of the implantable medical device of FIG. 1, showing a dielectric insulator sleeve slid around the elongated lead body core.
Figure 10C:
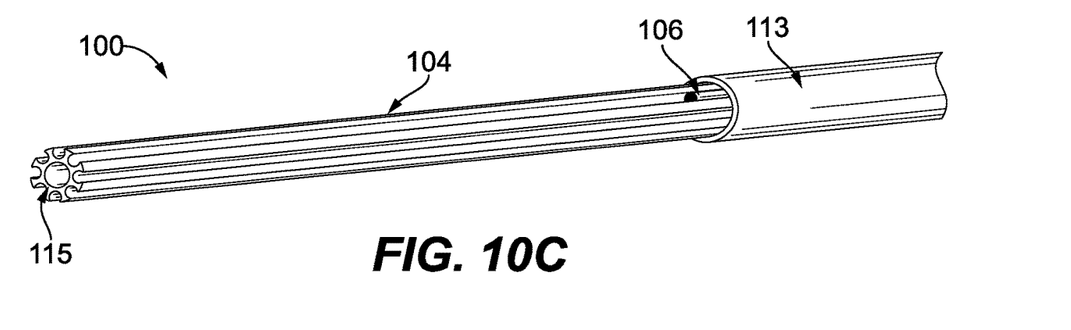
FIG. 10C is a schematic perspective view of a distal end portion of an elongated lead body core of the implantable medical device of FIG. 1, showing a respective electrical conductor being positioned in an axially extending channel of the elongated lead body core.
Figure 10D:
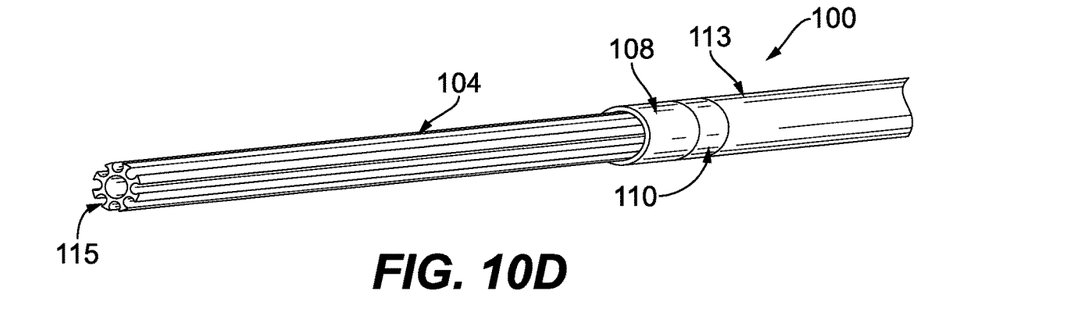
FIG. 10D is a schematic perspective view of a distal end portion of an elongated lead body core of the implantable medical device of FIG. 1, showing an electrode ring and dielectric insulator ring being stacked around the elongated lead body core.
Figure 10E:
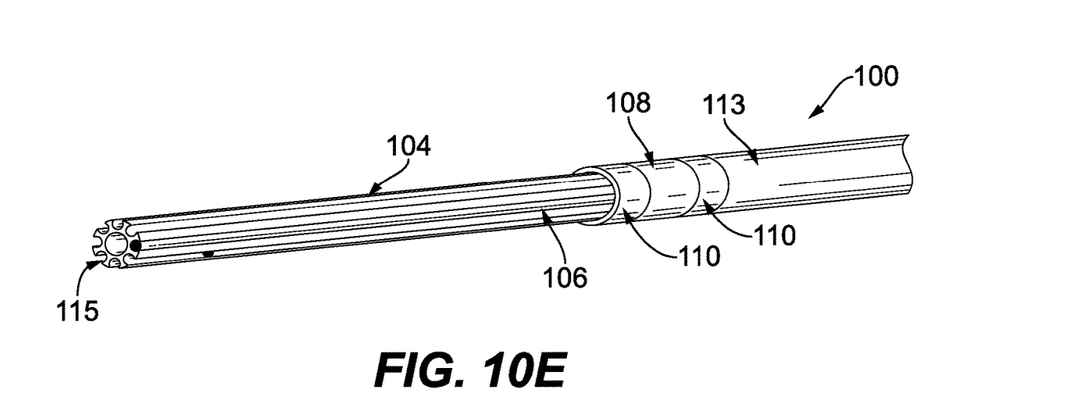
FIG. 10E is a schematic perspective view of a distal end portion of an elongated lead body core of the implantable medical device of FIG. 1, showing two electrode rings and dielectric insulator ring stacked around the elongated lead body core.

A method for manufacturing implantable lead 100 is shown in FIGS. 10A-10E. An embodiment of the method includes extruding elongated lead body core 104, shown in FIG. 10A, where elongated lead body core 104 includes axially extending channels 112 that are open, e.g. not enclosed. It is contemplated that elongated lead body core 104 can be molded, additively manufactured, or the like. The method includes positioning a dielectric insulator sleeve 113 around elongated lead body core 104, e.g. by sliding dielectric insulator sleeve 113 around elongated lead body core 104, shown in FIG. 10B. Respective electrical conductors 106 are then positioned in each of axially extending channels 112, one of which is shown in FIG. 10C. Embodiments of the method include positioning electrode rings 110 and dielectric insulator rings 108 around elongated lead body core 104, e.g. by sliding electrode rings 110 and dielectric insulator rings 108 around elongated lead body core 104, as shown in FIGS. 10D-10E. Sleeve 113 and rings 108 can similarly be extruded, molded, additively manufactured, or the like.

Figure 11:
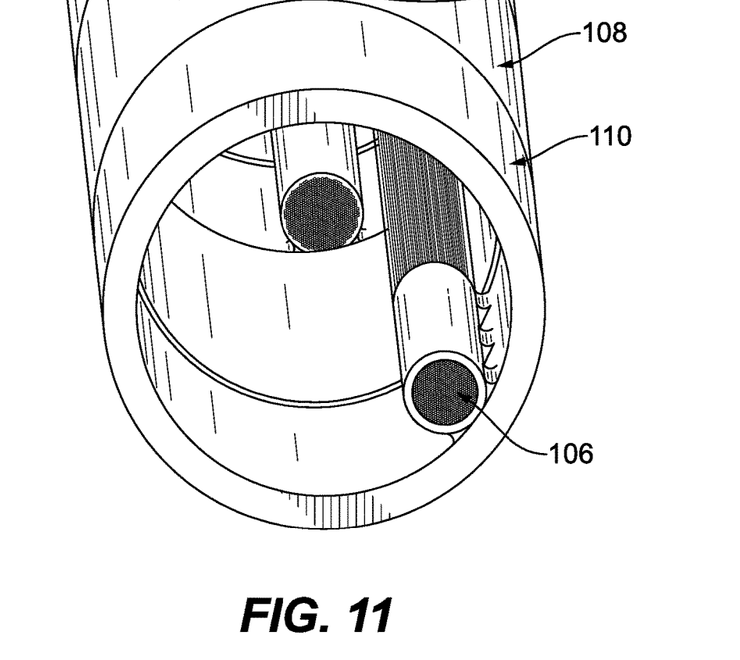
FIG. 11 is a schematic perspective view of a portion of the implantable medical device of FIG. 1 from the distal end, showing one of conductors being bonded to a respective electrode ring.

As shown in FIG. 11, after positioning one of electrode rings 110 embodiments of the method include bonding that electrode ring 110, to a respective conductor 106 by laser welding. Elongated lead body core 104 is not shown in FIG. 11 for sake of clarity. Laser welding can be repeated after the positioning of each electrode ring 100. Those skilled in the art will readily appreciate that while dielectric insulator rings 108 and electrode rings 110 are shown stacked in an alternating sequence, they can be stacked in a variety of suitable sequences. After insulator rings 108 and electrode rings 110 are stacked and cover body core 104 almost to its distal end 115, embodiments of the method include positioning dielectric end cap 102 on the distal end of the implantable lead 100, shown in FIG. 1. In accordance with some embodiments, heat, e.g., reflow, is applied after assembly of dielectric insulator rings 108, electrode rings 110 and end cap 102 onto lead body core 104.

With reference now to FIG. 12, proximal end 101 of lead 100 has a similar construction and is manufactured in a similar manner, e.g. by using the method described above with reference to FIGS. 10A-10E. Elongated lead body core 104 and conductors 106 (not shown, as they are covered over by dielectric insulator sleeve 113, electrode rings 110 and dielectric insulator rings 108) extend from a portion of lead 100 near distal end 103 to a portion of lead 100 near proximal end 101. The portion of insulator sleeve 113 that is shown in FIG. 12 is a proximal end portion of sleeve 113 shown in FIG. 1.

With continued reference to FIG. 12, one additional "anchor" electrode 117 is positioned between the proximal end of insulator sleeve 113 and one of dielectric insulator rings 108. Anchor electrode 117 can be positioned on core 104 by sliding anchor electrode 117 around elongated lead body core 104. Anchor electrode 117 is not electrically connected. In use, the active medical stimulator device (not shown) has a set screw that anchors into anchor electrode 117 to prevent proximal end 101 from separating from the active medical stimulator device. A second end cap 105 is positioned on proximal end 101 of lead 100. Second end cap 105 is different from end cap 102 in that it has a center opening 107 the same diameter as the inner central lumen of core 104 to facilitate the introduction of a stylet (not shown) that introduces implantable lead 100 into a patient and is then removed from lead 100 after implant. Once fully assembled, the entire implantable lead assembly 100 is reflowed (heated along length) to bond all components together, becoming one piece.

After re-flow, assembly 100 is run between two grinding wheels and centerless ground along its full length to polish an outer diameter to a smooth uniform outer diameter. While the method for manufacture is described herein in the context of implantable lead 100 it is contemplated that the method described herein can be applied to other embodiments of implantable leads, or the like.

The methods and systems of the present disclosure, as described above and shown in the drawings, provide for implantable medical devices, such as heart leads, neuro-sensing and neuro-stimulation devices, and intervention catheters and devices, manufactured in a manner that reduces manufacturing time and expense. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. An implantable lead, comprising:
a) an elongated lead body core comprising at least two ribs that are circumferentially spaced apart from each other by one of at least two open channels that extends axially along a longitudinal axis from a proximal end to a distal end of the lead body core, wherein each of the at least two ribs comprises an axially extending segmented cylindrically-shaped outer peripheral surface;
b) at least two electrical conductors;
c) at least two electrically conductive sleeves, wherein one of the sleeves is supported on a respective one of the at least two electrical conductors, and wherein one of the electrical conductors supporting a sleeve is positioned in a respective one of the at least two axially extending open channels adjacent to the segmented cylindrically-shaped outer peripheral surfaces of the at least two axially extending ribs;
d) at least two electrode rings supported on the lead body core so that an inner surface of the electrode rings faces the electrically conductive sleeve supported on a respective one of the at least two electrical conductors, wherein each of the at least two electrode rings has a cylindrically-shaped electrode ring inner surface that directly contacts the segmented cylindrically-shaped outer peripheral surfaces of the at least two axially extending ribs;
e) at least one dielectric insulator ring supported on the outer peripheral surface of the lead body core between the at least two electrode rings to prevent the electrode rings from contacting each other, wherein the dielectric insulator ring has a cylindrically-shaped insulator ring inner surface that directly contacts the segmented cylindrically-shaped outer peripheral surfaces of the at least two axially extending ribs;

f) a weld connecting the electrode ring inner surface of the at least two electrical rings to the electrically conductive sleeve supported on a respective one of the at least two electrical conductors; and g) a distal dielectric end cap supported on the distal end of the lead body core, h) wherein the distal dielectric end cap and the at least one dielectric insulator ring are heat bonded to the lead body core.

2. The implantable lead of claim 1, wherein the lead body core includes an inner central lumen.

3. The implantable lead of claim 2, wherein a proximal dielectric end cap is supported on the proximal end of the lead body core, and wherein the proximal dielectric end cap has a center opening that is in open communication with the inner central lumen in the lead body core.

4. The implantable lead of claim 1, wherein an outer diameter of the lead body core including the distal dielectric end cap is characterized as having been ground to a smooth uniform outer diameter.

5. The implantable lead of claim 1, wherein an anchor electrode is supported on the lead body core, and wherein the anchor electrode is not electrically connected to an electrical conductor.

6. The implantable lead of claim 5, wherein the anchor electrode is configured to connect the implantable lead to an external medical device.

7. The implantable lead of claim 5, further comprising a dielectric sleeve supported on the outer peripheral surface of the lead body core, wherein the anchor electrode is positioned between the dielectric sleeve and the at least one dielectric insulator ring.

8. An implantable lead, comprising:
a) an elongated lead body core having a plurality of ribs that extends axially along a longitudinal axis from a proximal end to a distal end of the lead body core and that are circumferentially spaced apart from each other around the longitudinal axis by an intermediate one of a plurality of axially extending open channels, wherein each rib comprises an axially extending segmented cylindrically-shaped outer peripheral surface;

b) a plurality of electrical conductors;

c) a plurality of electrically conductive sleeves, wherein one of the sleeves is supported on a respective one of the electrical conductors, and wherein one of the electrical conductors supporting a sleeve is positioned in a respective one of the axially extending open channels adjacent to the segmented cylindrically-shaped outer peripheral surfaces of immediately adjacent axially extending ribs;

d) a plurality of electrode rings supported on the outer peripheral surface of the lead body core so that an inner surface of each electrode ring faces the electrically conductive sleeve supported on a respective one of the plurality of electrical conductors, wherein each of the electrode rings has a cylindrically-shaped electrode ring inner surface that matches and directly contacts the segmented cylindrically-shaped outer peripheral surfaces of the plurality of axially extending ribs;

e) a plurality of dielectric insulator rings supported on the outer peripheral surface of the lead body core between two electrode rings to prevent the electrode rings from contacting each other, wherein each of the dielectric insulator rings has a cylindrically-shaped insulator ring inner surface that directly contacts the segmented cylindrically-shaped outer peripheral surfaces of the plurality of axially extending ribs;

f) a weld connecting the inner surface of a respective one of the electrical rings to the electrically conductive sleeve supported on a respective one of the plurality electrical conductors; and g) a distal dielectric end cap supported on the distal end of the lead body core, h) wherein the distal dielectric end cap and the plurality of dielectric insulator rings are heat bonded to the lead body core.

9. The implantable lead of claim 8, wherein the lead body core includes an inner central lumen.

10. The implantable lead of claim 9, further comprising a proximal dielectric end cap supported on the proximal end of the lead body core, wherein the proximal dielectric end cap has a center opening that is in open communication with the inner central lumen in the lead body core.

11. The implantable lead of claim 8, wherein an anchor electrode is supported on the lead body core, and wherein the anchor electrode is not electrically connected to an electrical conductor.

12. The implantable lead of claim 11, wherein the anchor electrode is configured to connect the implantable lead to an external medical device.

13. The implantable lead of claim 8, further comprising a dielectric sleeve supported on the outer peripheral surface of the lead body core.

14. The implantable lead of claim 8, further comprising a proximal dielectric end cap supported on the proximal end of the lead body core, the proximal dielectric end cap having a center opening, wherein the lead body core has an inner central lumen that is in open communication with the center opening in the proximal dielectric end cap.

15. A method for manufacturing an implantable lead, comprising the steps of:
a) extruding an elongated lead body core comprising a plurality of axially extending ribs that are circumferentially spaced apart from each other around a longitudinal axis by an intermediate one of a plurality of open channels, wherein each rib comprises a segmented cylindrically-shaped outer peripheral surface extending axially from a proximal end to a distal end of the lead body core;

b) providing a plurality of electrical conductors;

c) supporting an electrically conductive sleeve on a respective one of the plurality of electrical conductors and positioning the electrical conductor in a respective one of the axially extending open channels so that the conductive sleeve resides adjacent to the segmented cylindrically-shaped outer peripheral surfaces of immediately adjacent axially extending ribs;

d) providing a plurality of electrode rings and supporting the electrode rings on the outer peripheral surface of the lead body core so that an inner surface of each electrode ring faces the electrically conductive sleeve of a respective one of the electrical conductors, wherein each electrode ring has a cylindrically-shaped inner surface that matches and directly contacts the segmented cylindrically-shaped outer peripheral surfaces of each of the plurality of axially extending ribs; and e) supporting a plurality of dielectric insulator rings on the outer peripheral surface of the lead body core, each of the dielectric insulator rings having an inner surface that directly contacts the segmented cylindrically-shaped outer peripheral surfaces of the plurality of axially extending ribs, wherein one of the plurality of dielectric insulator rings is positioned between two of the plurality of electrode rings;

f) welding the electrode ring, inner surface of each of the electrode rings to the electrically conductive sleeve supported on a respective one of the plurality of electrical conductors;

g) positioning a distal dielectric end cap on the distal end of the lead body core; and h) heating the lead body core to bond the distal dielectric end cap and the plurality of dielectric insulator rings to the lead body core.

16. The method of claim 15, including:

a) supporting a proximal dielectric end cap on the proximal end of the lead body core; and b) providing an inner central lumen extending through the lead body core, wherein the proximal dielectric end cap has a center opening that is in open communication with the inner central lumen in the lead body core.

17. The method of claim 15, including grinding an outer diameter of the lead body core including the distal dielectric end cap to a smooth uniform outer diameter.

18. The method of claim 15, including supporting an anchor electrode on the lead body core, wherein the anchor electrode is not electrically connected to an electrical conductor.

19. The method of claim 18, including supporting a dielectric sleeve on the outer peripheral surface of the lead body core, wherein the anchor electrode supported on the lead body core is positioned between the dielectric sleeve and the at least one dielectric insulator ring.

* * * * *